(12) United States Patent
Louy et al.

(10) Patent No.: US 12,708,704 B2
(45) Date of Patent: Aug. 18, 2026

(54) SYSTEMS AND METHODS FOR SENSORLESS BLOCKAGE DETECTION IN A SURGICAL FLUID MANAGEMENT SYSTEM

(71) Applicant: Medtronic Xomed, LLC, Jacksonville, FL (US)

(72) Inventors: Paul M. Louy, Jacksonville, FL (US); Marius G. Urdareanu, Jacksonville, FL (US)

(73) Assignee: Medtronic Xomed, LLC, Jacksonville, FL (US)

( * ) Notice: Subject to any disclaimer, the term of this patent is extended or adjusted under 35 U.S.C. 154(b) by 714 days.

(21) Appl. No.: 18/131,683

(22) Filed: Apr. 6, 2023

(65) Prior Publication Data

US 2023/0372599 A1 Nov. 23, 2023

Related U.S. Application Data

(60) Provisional application No. 63/343,206, filed on May 18, 2022.

(51) Int. Cl.
*A61M 1/00* (2006.01)

(52) U.S. Cl.
CPC ................ *A61M 1/73* (2021.05); *A61M 1/74* (2021.05); *A61M 2205/332* (2013.01)

(58) Field of Classification Search
None
See application file for complete search history.

(56) References Cited

U.S. PATENT DOCUMENTS 4,256,437 A * 3/1981 Brown .................. A61M 5/142 417/63
5,242,404 A * 9/1993 Conley ................. A61M 1/743 604/35

(Continued)

FOREIGN PATENT DOCUMENTS

WO WO-2014168985 A1 * 10/2014 .......... A61M 3/0212

OTHER PUBLICATIONS

Derammelaere et al., Load angle estimation for two-phase hybrid stepping motors, published in IET Electric Power Applications. (Year: 2013).*

(Continued)

*Primary Examiner* — Manuel A Mendez
(74) *Attorney, Agent, or Firm* — Carter, DeLuca & Farrell, LLP

(57) ABSTRACT

A surgical fluid management system includes a fluid pump configured to pump fluid along a fluid flow path into or out of a surgical site, and a pump drive and control assembly operably coupled to the fluid pump. The assembly includes a stepper motor configured, in response to driving of the step motor, to provide a rotational output to drive the fluid pump; a driver configured to provide electrical drive pulses to the stepper motor to drive the stepper motor; and a controller configured to command the driver to provide the electrical drive pulses to the stepper motor. The controller is further configured to receive feedback from at least one of the stepper motor or the driver, evaluate an indicator of a load associated with the stepper motor, and determine whether a blockage condition associated with the fluid flow path exists based upon the evaluation of the indicator.

16 Claims, 4 Drawing Sheets

(56) References Cited

U.S. PATENT DOCUMENTS

| | | | |
|---|---|---|---|
| 8,339,092 | B2 | 12/2012 | Cox et al. |
| 8,852,085 | B2 | 10/2014 | Shener-Irmakoglu et al. |
| 9,770,541 | B2 | 9/2017 | Carr et al. |
| 2008/0097284 | A1 | 4/2008 | Gao et al. |

OTHER PUBLICATIONS

De Viaene et al., Load angle estimation for dynamic stepping motor motion applications. (Year: 2017).*

* cited by examiner

SYSTEMS AND METHODS FOR SENSORLESS BLOCKAGE DETECTION IN A SURGICAL FLUID MANAGEMENT SYSTEM

CROSS-REFERENCE TO RELATED APPLICATIONS

This application claims the benefit of, and priority to, U.S. Provisional Patent Application No. 63/343,206, filed on May 18, 2022, the entire contents of which are hereby incorporated herein by reference.

FIELD

The present disclosure relates to surgical fluid management and, more specifically, systems and methods for sensorless blockage detection in a surgical fluid management system.

BACKGROUND

Fluid is utilized in conjunction with many surgical devices, systems, and methods to facilitate performing a surgical task such as, for example, enabling irrigation at a treatment site, aspiration at a treatment site, cleaning of a surgical device, washing of a treatment site, clearing a field of view, cooling a surgical device, etc. Some non-limiting examples of surgical devices that benefit from the use of fluid include microdebriders, surgical drills, surgical saws, suction irrigators, tissue shavers, endoscopes, balloon or other catheters, energy devices, and the like.

Surgical systems enabling the use of fluid typically include a fluid management console connected to a surgical device. The fluid management console may further connect to a fluid source and/or fluid collection canister and incorporate a pump to enable control of the flow of fluid to the surgical site via the surgical device and/or from the surgical site via the surgical device or a separate outflow path.

SUMMARY

The terms “about,” substantially,” and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a surgical fluid management system including a fluid pump configured to pump fluid along a fluid flow path into or out of a surgical site, and a pump drive and control assembly operably coupled to the fluid pump. The pump drive and control assembly includes: a stepper motor configured, in response to driving of the step motor, to provide a rotational output to drive the fluid pump; a driver configured to provide electrical drive pulses to the stepper motor to drive the stepper motor; and a controller configured to command the driver to provide the electrical drive pulses to the stepper motor and to receive feedback from at least one of the stepper motor or the driver. The controller is further configured to evaluate an indicator of a load associated with the stepper motor, and determine whether a blockage condition associated with the fluid flow path exists based upon the evaluation of the indicator.

In an aspect of the present disclosure, the indicator is back electromotive force (EMF). In another aspect of the present disclosure, the indicator is load angle. In these or other aspects, the indicator is inversely proportional to the load associated with the stepper motor.

In another aspect of the present disclosure, the controller is configured to evaluate the indicator by comparing the indicator to a threshold.

In still another aspect of the present disclosure, in a case where the controller determines that the blockage condition exists, the controller is further configured to provide instructions to output at least one of an audible, tactile, or visual signal to indicate to a user that the blockage condition exits. Alternatively or additionally, in a case where the controller determines that the blockage condition exists, the controller is further configured to stop commanding the driver, thereby stopping operation of the stepper motor and the fluid pump.

In yet another aspect of the present disclosure, the surgical fluid management system further includes a surgical device operably coupled to the fluid flow path. In such aspects, the fluid pump may be configured to pump fluid along the fluid flow path, through the surgical device, and into the surgical site.

In still yet another aspect of the present disclosure, the surgical fluid management system further includes a fluid source. In such aspects, the fluid pump may be configured to pump fluid from the fluid source, along the fluid flow path, through the surgical device, and into the surgical site.

In another aspect of the present disclosure, the fluid pump is a peristaltic pump. A rotary pump or other suitable pump is also contemplated.

A method of surgical fluid management provided in accordance with the present disclosure includes driving a stepper motor to thereby drive a fluid pump to pump fluid along a fluid flow path into or out of a surgical site, evaluating an indicator of a load associated with the stepper motor, and determining whether a blockage condition associated with the fluid flow path exists based upon the evaluation of the indicator.

In an aspect of the present disclosure, evaluating the indicator includes evaluating back electromotive force (EMF). Alternatively or additionally, evaluating the indicator includes evaluating load angle.

In another aspect of the present disclosure, evaluating the indicator includes comparing the indicator to a threshold.

In still another aspect of the present disclosure, in a case where the blockage condition is determined to exist, the method further includes providing instructions to output at least one of an audible, tactile, or visual signal to indicate to a user that the blockage condition exits.

In yet another aspect of the present disclosure, in a case where the blockage condition is determined to exist, the method further includes stopping operation of the stepper motor, thereby stopping operation of the fluid pump.

In still yet another aspect of the present disclosure, driving the stepper motor includes commanding a driver to provide electrical drive pulses to the stepper motor.

In another aspect of the present disclosure, the method further includes receiving feedback associated with the driving of the stepper motor, and determining the indicator based at least in part upon the received feedback.

BRIEF DESCRIPTION OF THE DRAWINGS

Various aspects and features of the present disclosure are described hereinbelow with reference to the drawings wherein.

DETAILED DESCRIPTION

Figures 1, 2:
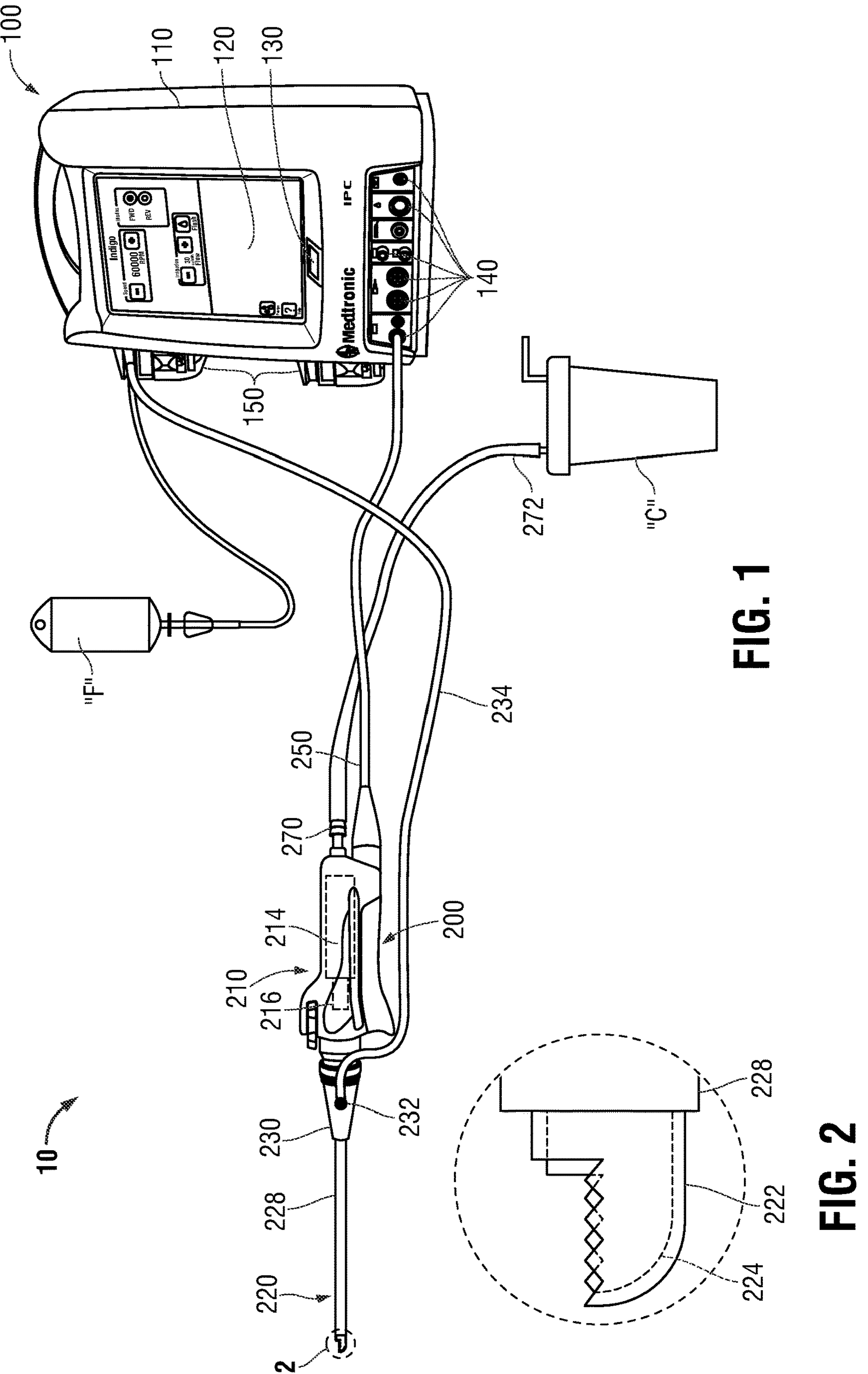
FIG. 1 is a perspective view of a surgical system provided in accordance with aspects of the present disclosure including a surgical device, a console, a fluid source, and a fluid collection canister.
FIG. 2 is an enlarged, perspective view of the area of detail indicated as "2" in FIG. 1.

Referring to FIG. 1, a surgical system 10 provided in accordance with the present disclosure generally includes: a console 100; one or more surgical devices 200 configured to be powered, controlled, energized, supplied fluid, and/or supplied vacuum by console 100; one or more fluid sources "F;" and/or one or more fluid collection canisters "C." Although plural surgical devices 200, fluid sources "F," and/or fluid collection canisters "C" are contemplated, surgical system 10 is described below with reference to only one of each of these features for purposes of brevity and understanding. Likewise, although console 100 may include plural identical or similar features to accommodate, for example, the plurality of surgical devices 200, fluid sources "F," and/or fluid collection canisters "C," each of these features is described in the singular hereinbelow for purposes of brevity and understanding.

Console 100 includes: an outer housing 110 enclosing the internal operable components of console 100; a graphical user interface (GUI) 120 (such as, for example, a touch screen GUI); an ON/OFF button 130; a plurality of device ports 140; one or more fluid pumps 150; and/or other suitable features. Console 100 further includes one or more controllers in the form of central processing units (CPU's) and/or microcontroller units (MCU's), power generating and control hardware, surgical energy generating and control hardware, and/or any other suitable hardware and corresponding firmware/software stored thereon for operating and controlling operation of surgical devices 200 connected thereto and the fluid pumps 150 thereof.

The one or more device ports 140 of console 100 may include, for example, power ports for powering and controlling connected powered surgical device(s), e.g., surgical device 200; energy ports for providing surgical energy, e.g., monopolar, bipolar, microwave, ultrasonic, thermal, light, and/or other surgical energy, to connected energy device(s); and/or auxiliary ports for connection of one or more auxiliary devices such as a foot switch.

The one or more fluid pumps 150 of console 100 may be similar or different from one another (where multiple fluid pumps 150 are provided) and each may be configured as a peristaltic pump (as shown), a rotary pump, or any other suitable pump configured to facilitate fluid irrigation and/or suction during a surgical procedure including cassette-based pumps. Console 100 additionally includes a pump drive and control assembly 300 (FIG. 3) associated with each fluid pump 150 and configured to drive and control the corresponding fluid pump 150, as detailed below.

Continuing with reference to FIG. 1, surgical device 200, as noted above, may be powered, controlled, energized, supplied fluid, and/or supplied vacuum by console 100. Surgical device 200 may be configured as, for example and without limitation, one or more of a microdebrider, surgical drill, surgical saw, suction irrigator, tissue shaver, endoscope, sheath for an endoscope (e.g., a lens cleaning sheath), balloon or other catheter, energy device, fluid cooled device, etc.

In aspects, surgical device 200 includes a handpiece 210 and an end effector 220 releasably engagable with handpiece 210. More specifically, with respect to surgical tissue removal devices, e.g., microdebriders, surgical drills, tissue shavers, etc., handpiece 210 may include a motor 214 disposed therein and a drive rotor 216 coupled to motor 214 and configured to drive a movable (e.g., rotational, reciprocating, oscillating, or combinations thereof) component of end effector 220 to remove tissue from a surgical site. With additional reference to FIG. 2, for example, end effector 220 may include an outer shaft 222 and an inner shaft 224 configured to be driven by motor 214 via drive rotor 216 to move relative to outer shaft 222 to cut tissue. Further, vacuum may be applied through outer shaft 222 and/or inner shaft 224, e.g., through an outflow fluid line 272 connected to collection cannister "C," to remove the cut tissue (along with fluid and debris) from the surgical site through outer shaft 222 and/or inner shaft 224 and to fluid collection canister "C." Surgical device 200 may also include a power cord 250 configured to connect surgical device 200 to a corresponding port 140 of console 100 to power and control motor 214, thereby controlling operation of end effector 220.

End effector 220 may additionally or alternatively include a sheath 228 disposed about (in fixed or removable fashion) outer shaft 222 and configured to deliver fluid to the surgical site. In such aspects, a proximal hub 230 disposed at the proximal end of sheath 228 may include a port 232 to connect to an inflow fluid line 234 (e.g., tube) to enable fluid to be pumped through sheath 228 and into the surgical site. Alternatively, port 232 may enable connection of a vacuum line such that sheath 228 may be used for withdrawing fluid from the surgical site. Other suitable configurations of surgical device 200 for treating tissue and/or of fluid supply/removal associated with surgical device 200 are also contemplated.

Referring back to FIG. 1, fluid source "F," e.g., an IV fluid bag, is fluidly coupled to sheath 228 of end effector 220 of surgical device 200 (or other suitable fluid inflow component) via inflow fluid line 234. Inflow fluid line 234 is operably coupled to one of the fluid pumps 150, e.g., received within the roller channel of a peristaltic fluid pump 150, to enable the pumping of fluid from fluid source "F" to end effector 220 of surgical device 200.

Fluid collection canister "C," in aspects where provided, is fluidly coupled to an outflow port 270 of surgical device 200 via an outflow fluid line 272 and, in aspects, is further coupled to a vacuum source, e.g., a vacuum pump associated with via console 100 or separate therefrom, to facilitate the withdrawal of fluid (and tissue, debris, etc.) from the surgical site, through surgical device 200, and into fluid collection canister "C."

Figure 3:
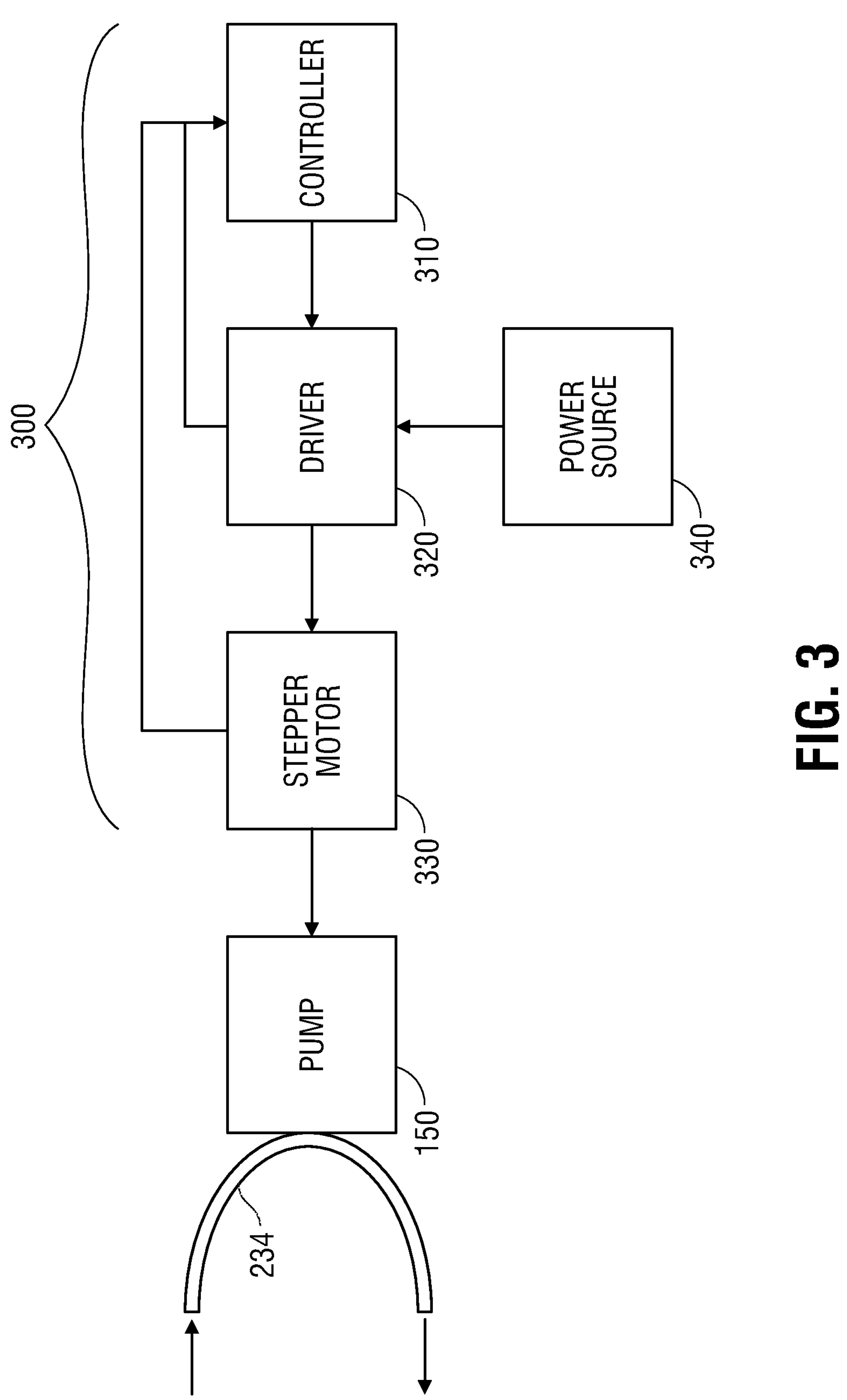
FIG. 3 is a block diagram of features of the console of the surgical system of FIG. 1.

With reference to FIG. 3, pump drive and control assembly 300 is configured to drive and control fluid pump 150 to thereby control the pumping of fluid into and/or out of a surgical site, e.g., the pumping of fluid from fluid source "F" (FIG. 1) into the surgical site via inflow flow line 234 operably coupled to fluid pump 150. Pump drive and control assembly 300 generally includes a controller 310, a driver 320, and a stepper motor 330. Controller 310 is configured to command driver 320, e.g., in response to user input to start fluid pump 150 (or user input to start surgical device 200 (FIG. 1), thereby signaling that fluid pump 150 should also be started), to drive stepper motor 330 to thereby operate fluid pump 150 in a desired manner. Driver 320, based on the commands received from controller 310, controls the sequence, frequency, and phase of the electrical drive pulses provided to stepper motor 330 such that the output rotor of stepper motor 330 is rotated through a plurality of angular steps in the commanded manner. Thus, by controlling the output rotor of stepper motor 330, fluid pump 150, which is driven by the output rotor of stepper motor 330, is thereby controlled in the commanded manner. A power source 340 powers pump drive and control assembly 300 and may be connected to a standard wall outlet, a battery of console 100, and/or may be any other suitable power source.

Figure 4:
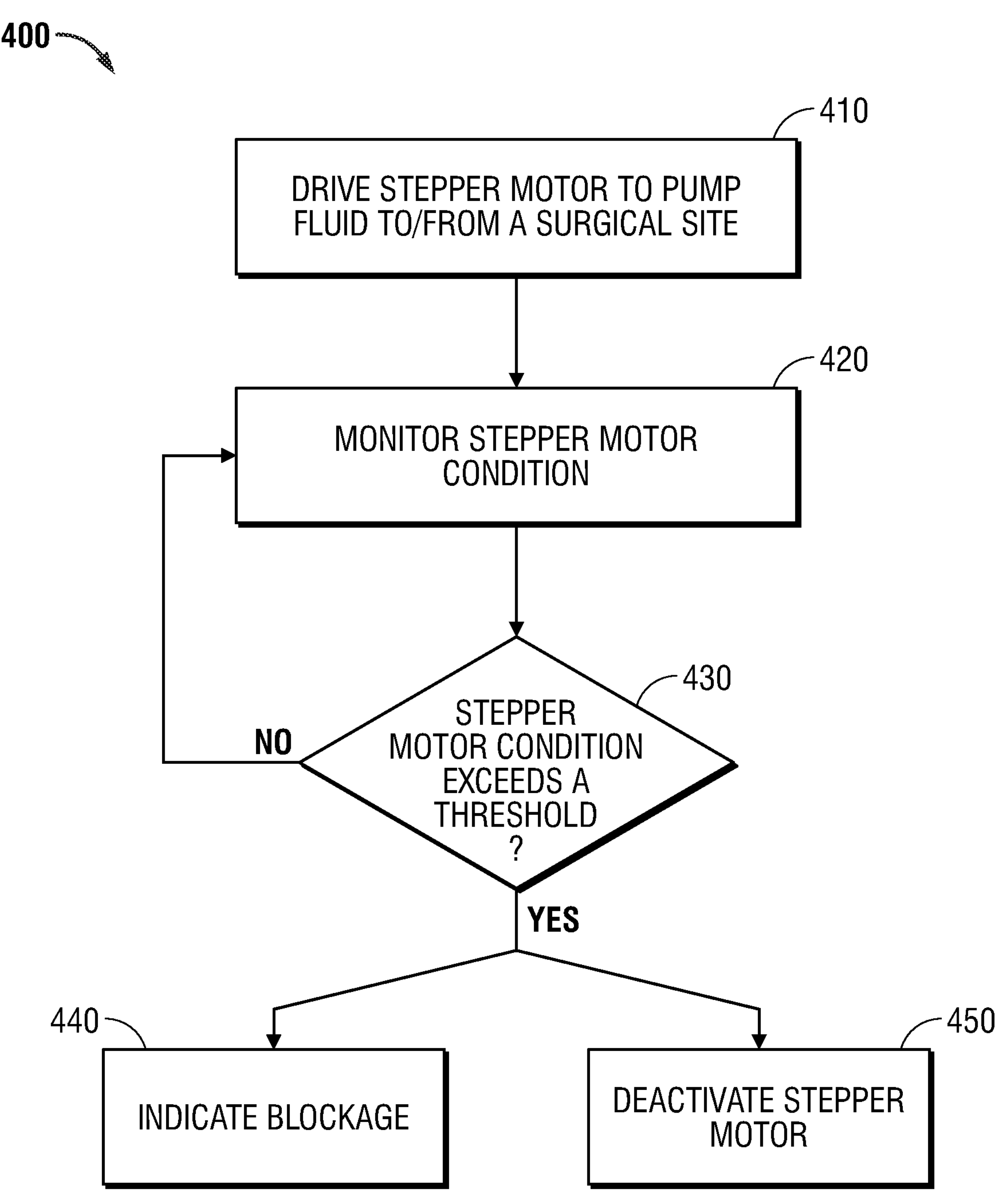
FIG. 4 is a flow diagram of a method in accordance with aspects of the present disclosure.

Referring also to FIG. 4, a method 400 in accordance with the present disclosure begins at 410 wherein stepper motor 330 is driven to operate fluid pump 150 to pump fluid into and/or out of a surgical site, e.g., as detailed above. During operation of stepper motor 330, controller 310 monitors the condition of stepper motor 330, as indicated at 420. However, determining a condition of stepper motor 330, such as the load associated with stepper motor 330, is not easily measured or determined without the use of a sensor, which adds cost and complexity to the system. In accordance with the present disclosure, in order to avoid the need for a sensor while still enabling monitoring of the condition of stepper motor 330, feedback data from driver 320 and/or stepper motor 330, e.g., commanded positions/angles, phase currents, and voltages, is utilized to determine an indicator of at least one condition of stepper motor 330, such as load associated with stepper motor 330. One such indicator of load of stepper motor 330 is back electromotive force (back EMF), which itself may be utilized or which may be utilized to determine torque and/or load angle, which are also indicative of the load of stepper motor 330. Back EMF of stepper motor 330 may be determined as described in U.S. Pat. No. 8,339,092, titled "Output Contact for Feedback in Integrated Circuit Motor Driver," the entire contents of which are hereby incorporated herein by reference, or in any other suitable manner. Other suitable sensorless indicators of at least one condition of stepper motor 330, such as load associated with stepper motor 330, are also contemplated. For example, in aspects, load angle is separately determined and utilized as the indicator of load of stepper motor 330.

Continuing with reference to FIGS. 3 and 4, back EMF is proportional to the rotational speed of stepper motor 330 and inversely proportional to the load associated with stepper motor 330. As such, for a higher load (e.g., a higher load torque or load angle), the back EMF is lower. Using this relationship, the back EMF determined in the monitoring indicated at 420 can be compared to a threshold at 430 to determine whether the back EMF exceeds the threshold (it is noted that the term "exceeding a threshold" as utilized herein is not limited to crossing an upper threshold; rather, for an indicator such as back EMF that is inversely proportional to the load, crossing below the threshold also constitutes exceeding the threshold). The threshold may be an absolute value, e.g., a specific voltage value, a relative differential value, e.g., a voltage difference between the present back EMF voltage value and one or more prior back EMF voltages values (which may be averaged or weighed in any other suitable manner), combinations thereof, or any other suitable threshold value, values, algorithm(s), etc.

A high load associated with stepper motor 330 is indicative of a potential issue with fluid pump 150 such as a blockage in the fluid flow path associated with fluid pump 150. Such a blockage may be the result of pinched or kinked tubing, an obstruction within or at an end of the tubing, an obstruction within or at fluid opening of a surgical device connected to the fluid flow path, a (partially or fully closed) valve, an unexpected pressure or pressure differential, etc. Thus, comparing the back EMF to the threshold at 430, in aspects, enables determination of whether a blockage is present in the fluid flow path associated with fluid pump 150.

Where the determined back EMF does not exceed the threshold, "NO" at 430, no blockage is present in the fluid flow path associated with fluid pump 150 and the method returns to 420 for continued monitoring during further operation of stepper motor 330 to drive fluid pump 150 as commanded. If, however, the determined back EMF exceeds the threshold, "YES" at 430, a blockage may be present in the fluid flow path associated with fluid pump 150 and, thus, the method proceeds to 440, where controller 310 instructs output of a signal indicating a potential blockage in fluid line 234 or otherwise along the fluid path associated with fluid pump 150 to be provided. Alternatively or additionally, if the determined back EMF exceeds the threshold, "YES" at 430, controller 310 deactivates stepper motor 330 to stop fluid pump 150 and inhibit further pumping of fluid via fluid pump 150. With respect to the signal output at 440, such signal may be an audible signal (e.g., an audible tone or series of tones output from a speaker of console 100), a tactile signal (e.g., haptic feedback provided from a vibration generator of surgical device 200 (FIG. 1) or other component of surgical system 10 (FIG. 1)), and/or a visual signal (e.g., a warning graphic, text, color change, flashing, etc. provided on GUI 120 of console 100 (FIG. 1)). Other suitable actions in response to determining a blockage is present in the fluid flow path associated with fluid pump 150 are also contemplated.

In aspects where both a signal is output at 440 and stepper motor 330 is deactivated at 450, the same or different thresholds may be utilized. With respect to different thresholds, a first threshold may trigger the signal at 440 and, thereafter, if the back EMF continues to excur and reaches a second threshold, stepper motor 330 may then be deactivated at 450. In these and other aspects, the threshold(s) may include temporal aspects. For example, exceeding the threshold may require exceeding a threshold value for at least a pre-determined period of time. In aspects where both a signal is output at 440 and stepper motor 330 is deactivated at 450, for example, the threshold values and/or pre-determined periods of time may be the same or different. With respect to different periods of time, exceeding the threshold for a first period of time (or exceeding the threshold at all) may trigger the signal at 440 and, thereafter, continuing to exceed the threshold for a second, greater period of time may trigger deactivation of the stepper motor 330 at 450.

Figure 5:
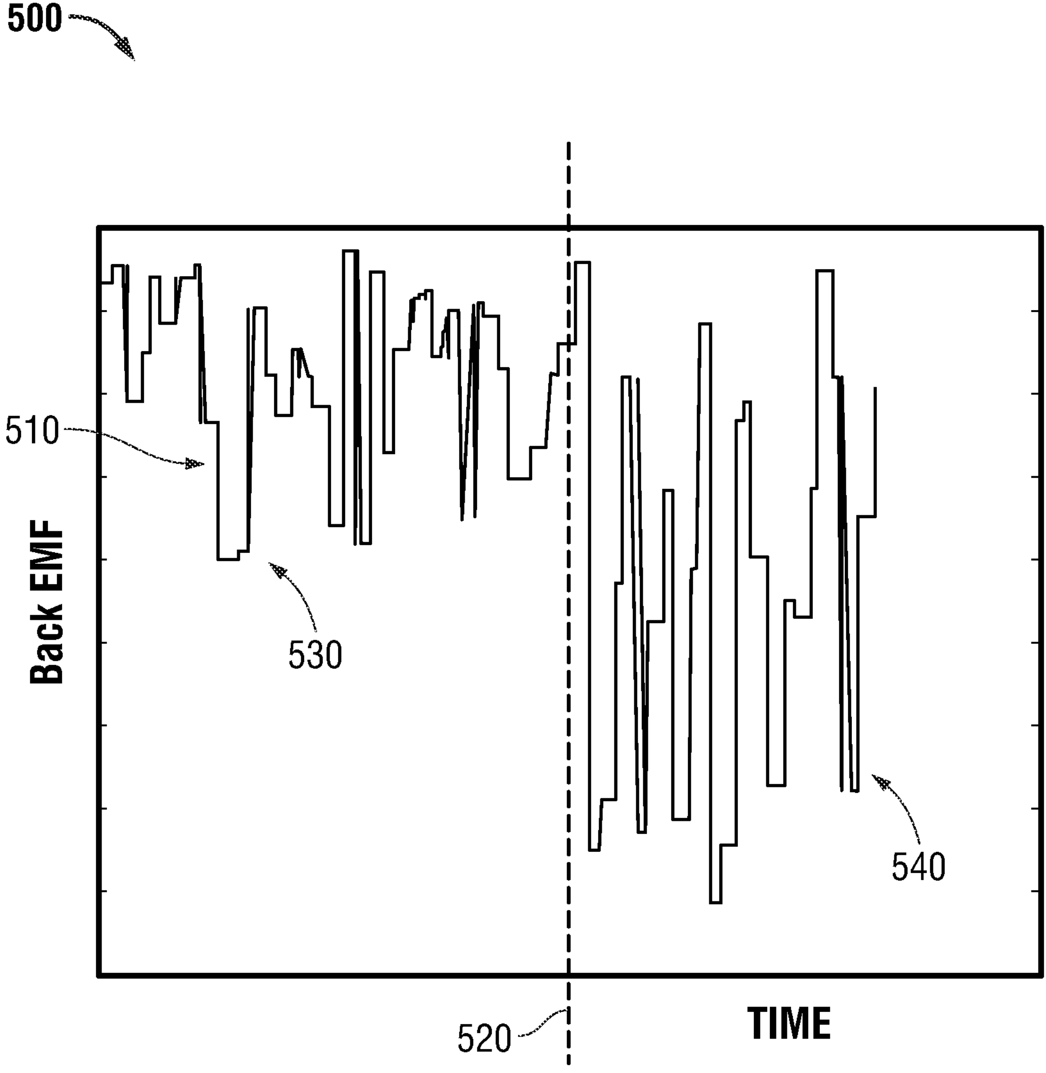
FIG. 5 is a graph illustrating back electromotive force (EMF) as a function of time for a stepper motor driving a fluid pump.

With reference to FIG. 5, an exemplary graph 500 illustrates a plot 510 of back EMF as a function of time, e.g., back EMF of stepper motor 330 driving fluid pump 150 (see FIG. 3). Graph 500 is exemplary in nature and provided for illustration purposes, thus, units are not included. Indicated on graph 500 is a blockage event 520 that has occurred at a particular point in time. As can be seen from graph 500, the portion 530 of plot 510 of back EMF as a function of time prior to the blockage event 520, e.g., where no blockage was present, differs from the portion 540 of plot 510 of back EMF as a function of time after the blockage event 520 has occurred, e.g., while the blockage was present. More specifically, given that back EMF is inversely proportional to load and that the load associated with stepper motor 330 increases when a blockage event 520 is encountered, the drop in back EMF signifies the presence and timing of the blockage event 520.

Referring generally to FIGS. 1-5, in aspects, back EMF and/or other indicators of load associated with stepper motor 330 may be utilized to detect other conditions of fluid pump 150 and/or system 10. For example, a detected rise in back EMF (e.g., exceeding a threshold), may indicate a lack of fluid (or insufficient fluid), a lack of fluid pressure, a lack of resistance, etc., which may be indicative of an empty fluid source, disconnected tubing, leakage, and/or other problems associated with fluid pump 150 and/or system 10.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A surgical fluid management system, comprising:

a fluid pump configured to pump fluid along a fluid flow path into or out of a surgical site; and a pump drive and control assembly operably coupled to the fluid pump, the pump drive and control assembly including:

a stepper motor configured, in response to driving of the stepper step motor, to provide a rotational output to drive the fluid pump;

a driver configured to provide electrical drive pulses to the stepper motor to drive the stepper motor; and a controller configured to command the driver to provide the electrical drive pulses to the stepper motor and to receive feedback from at least one of the stepper motor or the driver, the controller further configured to:

evaluate an indicator of a load associated with the stepper motor against a first threshold and a second threshold;

determine that a blockage condition associated with the fluid flow path exists based upon the indicator exceeding the first threshold; and determine that a loss or lack of fluid condition associated with the fluid flow path exists based upon the indicator exceeding the second threshold.

2. The surgical fluid management system according to claim 1, wherein the indicator is back electromotive force (EMF).

3. The surgical fluid management system according to claim 1, wherein the indicator is load angle.

4. The surgical fluid management system according to claim 1, wherein the indicator is inversely proportional to the load associated with the stepper motor.

5. The surgical fluid management system according to claim 1, wherein, in a case where the controller determines that the blockage condition or the loss or lack of fluid condition exists, the controller is further configured to provide instructions to output at least one of an audible, tactile, or visual signal to indicate to a user that the blockage condition or the loss or lack of fluid loss condition, respectively, exists.

6. The surgical fluid management system according to claim 1, wherein, in a case where the controller determines that the blockage condition or the loss or lack of fluid condition exists, the controller is further configured to stop commanding the driver, thereby stopping operation of the stepper motor and the fluid pump.

7. The surgical fluid management system according to claim 1, further comprising:

a surgical device operably coupled to the fluid flow path, wherein the fluid pump is configured to pump fluid along the fluid flow path, through the surgical device, and into the surgical site.

8. The surgical fluid management system according to claim 7, further comprising:

a fluid source, wherein the fluid pump is configured to pump fluid from the fluid source, along the fluid flow path, through the surgical device, and into the surgical site.

9. The surgical fluid management system according to claim 1, wherein the fluid pump is a peristaltic pump.

10. A method of surgical fluid management, comprising:

driving a stepper motor to thereby drive a fluid pump to pump fluid along a fluid flow path into or out of a surgical site;

evaluating an indicator of a load associated with the stepper motor against a first threshold and a second threshold;

determining that a blockage condition associated with the fluid flow path exists based upon the indicator exceeding the first threshold; and determining that a loss or lack of fluid condition associated with the fluid flow path exists based upon the indicator exceeding the second threshold.

11. The method according to claim 10, wherein evaluating the indicator includes evaluating back electromotive force (EMF).

12. The method according to claim 10, wherein evaluating the indicator includes evaluating load angle.

13. The method according to claim 10, wherein, in a case where the blockage condition is determined to exist or wherein the loss or lack of fluid condition is determined to exist, the method further includes:

providing instructions to output at least one of an audible, tactile, or visual signal to indicate to a user that the blockage condition or the loss or lack of fluid condition, respectively, exists.

14. The method according to claim 10, wherein, in a case where the blockage condition is determined to exist or wherein the loss or lack of fluid condition is determined to exist, the method further includes:

stopping operation of the stepper motor, thereby stopping operation of the fluid pump.

15. The method according to claim 10, wherein driving the stepper motor includes:

commanding a driver to provide electrical drive pulses to the stepper motor.

16. The method according to claim 10, further comprising:

receiving feedback associated with the driving of the stepper motor; and determining the indicator based at least in part upon the received feedback.

* * * * *